United States Patent
Ye et al.

(10) Patent No.: US 9,677,133 B2
(45) Date of Patent: *Jun. 13, 2017

(54) BIOLOGICAL CHIP HYBRIDIZATION SYSTEM

(75) Inventors: Jiaming Ye, Beijing (CN); Pinhong Wang, Beijing (CN); Guoqing Wang, Beijing (CN); Liqing Duan, Beijing (CN); Kaijun Zhao, Beijing (CN); Jinxiu Zhang, Beijing (CN); Xiumei Song, Beijing (CN); Dong Wang, Beijing (CN); Huafang Gao, Beijing (CN); Wanli Xing, Beijing (CN)

(73) Assignees: CAPITALBIO CORPORATION, Beijing (CN); TSINGHUA UNIVERSITY, Beijing (CN)

(*) Notice: Subject to any disclaimer, the term of this patent is extended or adjusted under 35 U.S.C. 154(b) by 796 days.

This patent is subject to a terminal disclaimer.

(21) Appl. No.: 14/006,540

(22) PCT Filed: Feb. 10, 2012

(86) PCT No.: PCT/CN2012/071000
§ 371 (c)(1),
(2), (4) Date: Sep. 20, 2013

(87) PCT Pub. No.: WO2012/126294
PCT Pub. Date: Sep. 27, 2012

(65) Prior Publication Data
US 2014/0011707 A1    Jan. 9, 2014

(30) Foreign Application Priority Data
Mar. 22, 2011   (CN) .......................... 2011 1 0069012

(51) Int. Cl.
*C12Q 1/68* (2006.01)
*G01N 33/50* (2006.01)
(Continued)

(52) U.S. Cl.
CPC .......... *C12Q 1/6876* (2013.01); *B01L 3/5027* (2013.01); *B01L 7/52* (2013.01);
(Continued)

(58) Field of Classification Search
None
See application file for complete search history.

(56) References Cited

U.S. PATENT DOCUMENTS

| 6,391,623 B1 | 5/2002 | Besemer et al. |
| 2006/0154360 A1* | 7/2006 | Lee et al. ............ B01F 13/0059 |
| | | 435/287.2 |
| 2011/0017244 A1 | 1/2011 | Lau et al. |

FOREIGN PATENT DOCUMENTS

| CN | 1523354 | 8/2004 |
| CN | 1815233 | 8/2006 |

(Continued)

OTHER PUBLICATIONS

International Search Report from International Application No. PCT/CN2012/071000 mailed May 17, 2012.
(Continued)

*Primary Examiner* — Kaijiang Zhang
(74) *Attorney, Agent, or Firm* — Merchant & Gould P.C.

(57) ABSTRACT

A hybridization system is provided, which comprises a biological chip having a substrate (1) with a probe dot matrix (3) and a cover plate (2) with at least two through-holes (4), where a hybrid chamber (5) is formed between the substrate (1) and the cover plate (2), at least two fluid channels (6) are interconnected respectively with the hybrid chamber (5) by the two through-holes (4), and a fluid control device is interconnected with the fluid channels (6). The biological chip hybridization system integrates hybridizing, cleaning and drying functions, uses power provided by the fluid control device as the drive force for promoting the liquid flow for automatically reciprocation flow in the fluid chan-
(Continued)

nels (6) and the chamber (5) to achieve a dynamic hybridization, thus improving the hybrid efficiency and uniformity, and achieving automatic control.

20 Claims, 5 Drawing Sheets

(51) Int. Cl.
G01N 33/543 (2006.01)
B01L 3/00 (2006.01)
B01L 7/00 (2006.01)
G01N 35/00 (2006.01)

(52) U.S. Cl.
CPC ......... B01L 2300/0636 (2013.01); B01L 2300/0816 (2013.01); B01L 2300/0887 (2013.01); B01L 2300/1822 (2013.01); B01L 2300/1827 (2013.01); B01L 2300/1844 (2013.01); B01L 2400/0622 (2013.01); G01N 33/543 (2013.01); G01N 2035/00158 (2013.01)

(56) References Cited

FOREIGN PATENT DOCUMENTS

| CN | 101948741 | 1/2011 | |
|---|---|---|---|
| CN | 102199529 | 9/2011 | |
| JP | 2009-122022 | 6/2009 | |
| TW | 200642946 | 12/2006 | |
| TW | 200808963 | 2/2008 | |
| WO | WO 2009136892 A1 * | 11/2009 | .......... B01J 19/0046 |
| WO | WO 2010/149292 | 12/2010 | |

OTHER PUBLICATIONS

Lee et al., "Recirculating flow accelerates DNA microarray hybridization in a microfluidic device", *Lab Chip*, vol. 6, 2006, pp. 1163-1170.

Liu et al., "Enhanced Signals and Fast Nucleic Acid Hybridization by Microfluidic Chaotic Mixing", *Angew. Chem. Int. Ed.*, vol. 45, 2006, pp. 3618-3623.

* cited by examiner

BIOLOGICAL CHIP HYBRIDIZATION SYSTEM

This application is a National Stage Application of PCT/CN2012/071000, filed Feb. 10, 2012, which claims the benefit of China Patent Application No. 201110069012.6, filed with the Patent Office of China on Mar. 22, 2011, titled "Biological chip hybridization system", and which applications are incorporated herein by reference. To the extent appropriate, a claim of priority is made to each of the above disclosed applications.

FIELD OF THE INVENTION

The present invention relates to a hybridization system, particularly to a biological chip hybridization system in which hybridization reaction, cleaning and drying are integrated.

BACKGROUND OF THE INVENTION

The bio-chip is formed by sequentially immobilizing a great number of probe molecules with known sequence onto a support with high density by virtue of microfabrication or microelectronic technique. The probe molecules can be DNA, RNA, protein, sugar, etc. By detecting whether the probe is hybridized with the target species in the sample, gene expression characteristics, genetic defects, protein distribution, response characteristics, etc. can be analyzed.

The analytical method based on bio-chip mainly comprises the steps of sample pretreatment, chip preparation, chip hybridization, chip cleaning and drying, chip detection, etc. At present, there are comparatively advanced techniques and supporting instruments for the preparation and detection of bio-chip. For example, for the most popular glass-based bio-chip, a microarrayer can be used for microarray preparation, and detection thereof can also be performed on a corresponding chip scanner. Besides the chip preparation and detection, the chip cleaning and drying in the process of chip hybridization are one of the most important aspects for the bio-chip technique, and how to improve the controllability and accuracy of the hybridization process has become the major direction and hotspot for the bio-chip technique.

For traditional chip hybridization, a static hybridization method is generally employed with the temperature controlled by air bath or water bath. In such a method, since the hybridization reaction between the target molecules in the hybridization sample and the probe molecules on the chip surface only depends on molecular diffusion mechanism, it tends to require relatively long reaction duration and has low hybridization efficiency, and furthermore, readily results in homogenous hybridization over the whole chip, which is not favorable for quantitative analysis. Besides, after the completion of the hybridization, special cleaning and drying instruments or devices are additionally required for the cleaning and drying of the chip, which is quite complicated. In order to overcome disadvantages of the static hybridization, some dynamic hybridization methods and devices have already been proposed based on vibration mixing, continuous flow or reciprocating flow. For example, a dynamic hybridization method, in which a peristaltic pump is employed to force the hybridization sample to flow circularly over the surface of the microarray, has been proposed by Lee et al., by which method the hybridization duration is reduced from 6 hours of the static hybridization to 2 hours (See, H. H. Lee, J. Smoot, Z. McMurray, D. A. Stahl, P. Yager, Lab Chip, 2006, 6, 1163-1170).

Based on similar principle of circulation flow hybridization, an American company Affymetrix (U.S. Pat. No. 6,391,623) has developed an automatic hybridization system. Although integration of hybridization, cleaning and drying can be realized in such a system, large volume of sample are required in one hand, and on the other hand, interior contamination of pump will be easily resulted, due to the use of peristaltic pump and circulating fluid channel. Furthermore, the slot on the device is only available for the chip purchased from Affymetrix, that is the device is not compatible and versatile. Pneumatic-activated microvalve in PDMS (polydimethyl siloxane) microfluidic chip is utilized by Quake's group to achieve reciprocating movement of the hybridization sample solution in the hybridization chamber, and thereby the reaction rate and hybridization signal are significantly enhanced. (J. Liu, B. A. Williams, R. M. Gwirtz, B. J. Wold, S. Quake, Angew. Chem. Int. Ed. 2006, 45, 3618-3623).

By applying similar principle, reciprocating flow hybridization is realized by the NimbleGen Mixers hybridization instrument developed by Roche NimebleGen employing bubbles generated by a pneumatic valve, through which the detection sensitivity is enhanced by 3 folds, and the hybridization duration is reduced. However, the instrument only has the function for hybridization reaction, and special equipments are respectively required for the chip cleaning and drying, so that the hybridization, cleaning and drying can not be integrated.

Based on the description above, the present biological chip hybridization system has disadvantages such as long hybridization duration and low efficiency, or complicated operational procedure and low integration and automation level.

SUMMARY OF THE INVENTION

Based on the problems mentioned above, the objective of the present invention is to provide a biological chip hybridization system in which hybridization, cleaning and drying are integrated, comprising:

a bio-chip, which is formed by a substrate with probe array and a cover plate with at least two through holes, so that a hybridization chamber is formed between the substrate and the cover plate;

at least two fluid channels, which are connected to the hybridization chamber respectively through said two through holes;

a fluid control device, which is connected to the fluid channel.

During operation, at least one of the fluid channels is used as the fluid entrance channel, and the other as the fluid exit channel.

As a preference, the fluid control device comprises at least one pump for providing gas pressure, and one valve for controlling the flow of fluid, wherein the pump is connected to the fluid channel through the valve, which can be optionally connected through the valve to the fluid channel used as the fluid entrance channel, or to the fluid channel used as the fluid exit channel. Main functions of the fluid control device is to control the following procedures: reciprocating flow of the sample solution over the surface of probe array in order to achieve the dynamic hybridization reaction, continuous flow of the cleaning liquid over the surface of probe array in order to achieve the chip cleaning, continuous flow of inert gas into the hybridization chip in order to discharge the waste liquid, continuous flow of inert gas over the surface of probe array in order to achieve the dryness of the chip.

The pump mainly comprises the fluid driving pump used to control the reciprocating flow of the sample solution, the fluid driving pump used to control the continuous flow of the cleaning liquid and the fluid driving pump used to control the continuous flow of the drying gas. Any pump that increases or reduces the pressure in the air channel by using electrical signal can be used in the present invention. However, the fluid driving pump used to control the reciprocating flow of the sample solution is preferably the stepping motor syringe pump or plunger pump with the control precision in the range of micron unit volume, which can provide precise control of back-and-forth movement for the fluid (including gas and liquid) in the corresponding channel; the fluid driving pump used to control the continuous flow of cleaning liquid is preferably the piezoelectric micropump allowing the continuous flow of fluid, which provides continuous and stable flow of the liquid and is able to accurately control the flow rate of the liquid.

The fluid driving pump for the continuous flow of the drying gas is preferably the air pump with relatively large range of flow rate, which provides continuous, stable and high speed flow of gas.

The valve can be an interior valve integrated inside the flow path, or can be an exterior valve. Preferably, the micro-electromagnetic valve with less dead volume is selected, but is not limited thereto.

The pump and valve of the biological chip hybridization system provided in the present invention possess functions to fulfill the control of hybridization, cleaning and drying process of the chip, the specific number of which can be varied based on the design of the flow path. One pump and one valve can be used for each flow path, or alternatively, one pump can be shared by a plurality of flow paths, whereas one valve is used for each flow path to control the connection and disconnection of the flow path. When one valve of them is open while the others are close, the fluid controlled by this valve flows with the power provided by the pump. The valve can comprise a root valve to control the supply of fluid to the hybridization chamber. The root valve refers to a valve connected to a plurality of channels. Under such a circumstance, each channel can be opened or closed separately. Any pump that increases or reduces the pressure in the air channel by using electrical signal can be used in the present invention. However, it is preferable to use the stepping motor micropump with the control precision in the range of micron unit volume.

As a preference, the biomolecule of the bio-probe array of the bio-chip substrate of the biological chip hybridization system can be selected from the group consisting of, but not limited to: DNA, RNA, PNA (peptide nucleic acid), LNA (locked nucleic acid), peptide and protein.

The material for the bio-chip substrate and cover plate can be selected from the group consisting of glass, silicon and high molecular polymers such as PMMA (polymethyl methacrylate), PDMS (polydimethyl siloxane), PC (polycarbonate), PET (polyethylene terephthalate) and COC (cycloolefin copolymers), etc.

In particular examples of the present invention, a reciprocating flow based bio-chip is provided, which is formed by the cover plate, the microfluidic layer and the substrate through sealing, wherein the cover plate has at least two through holes, and the microfluidic layer has one hollow-out hybridization chamber and at least two hollow-out microfluidic channels, with one end of each microfluidic channel connected to the hybridization chamber, and the other end connected to one through hole of the cover plate, respectively, and the hybridization chamber of the microfluidic layer connected to the bio-probe array of the substrate.

As a preference, the cross-sectional area of the microfluidic channel of the microfluidic layer is in the range of 0.01-10 $mm^2$, and the length is in the range of 1 mm-100 mm.

The hybridization chamber provides space for reciprocating flow of the solution, the position and shape of which must ensure the uniformity of the reaction between the sample solution and the bio-probe on the lower layer substrate; the through hole is connected to the hybridization chamber via the microfluidic channel, and the solution stream is forced by the gas pressure generated by the syringe pump or plunger pump to flow back and forth in the microfluidic channel and hybridization chamber through the through hole. The reciprocating frequency of the reciprocating flow is preferably in the range of 0-100 Hz, and the gas pressure providing the driving force for the reciprocating flow is preferably in the range of 0-1 MPa.

More preferably, the lower surface of the cover plate, i.e., the surface sealed with the microfluidic layer, is hydrophilic, and most preferably, the surface of the cover plate contacted with the microfluidic layer has a contact angle of less than 90 degrees with respect to the sample solution, while the contact angle of the other side with respect to the sample solution is in the range of 90-180 degrees. When the sample is loaded at the through hole of the cover plate, the sample solution can enter and fill the hybridization chamber and the microfluidic channel automatically by using the liquid surface tension as the driving force.

More preferably, the biological chip hybridization system according to the present invention further comprises a temperature control device.

The temperature control device comprises hot plate, heating body, cooling body, temperature sensor and temperature controller.

The material for the hot plate can be metal or alloy, and also can be non-metallic materials with large coefficient of heat conductivity, such as silicon or glass. The hot plate is used for placing the chip and conducting the heat, the temperature control mode thereof can be temperature control of the upper surface or the lower surface.

Particularly, the heating body can be devices such as resistance wire, resistance membrane or Peltier.

Particularly, the cooling body can be devices such as radiator fan, and semiconductor refrigerator.

The temperature sensor and temperature controller can be a commercial temperature sensor and temperature controller, and also can be a control circuit, which is used for controlling the increase or decrease of the chip temperature or keeping the chip temperature constant.

The biological chip hybridization system provided in the present invention further comprises a fluid storage device connected to the fluid channel. The fluid storage device is a container such as a glass bottle or a plastic bottle, or a chip with fluid cavity, which is used for storage of various kinds of fluids required during the bio-chip detection process. The fluids include: the cleaning liquid used for chip cleaning after hybridization, and the fluid used for discharging the waste liquid and for chip drying. The fluid used for discharging the waste liquid and for chip drying is a gas or liquid which will not diffuse, dissolve in, and react with the sample solution and the cleaning liquid, and said fluid is preferably inert gases, which can be air or nitrogen gas. The entrance and exit of the sample solution, cleaning liquid and inert gas can be provided by the fluid channel.

As a preference, the biological chip hybridization system according to the present invention further comprises a control circuit. The control circuit is a single-chip microcomputer system, which automatically controls open and close of the valve, operation of the pump and the temperature of the heater.

More preferably, the biological chip hybridization system according to the present invention further comprises a monitor used for displaying the system operation.

The biological chip hybridization system provided in the present invention utilizes the fluid control device for power supply. In particular embodiments of the present invention, the liquid stream is forced to flow back and forth automatically in the hybridization channel and chamber under the gas pressure provided by the pump valve device, so as to achieve a dynamic hybridization reaction, and thereby enhance the efficiency and uniformity of the hybridization. Functions including chip hybridization, cleaning and drying are integrated in this system, and the sequence as well as the operation duration of various functions can be automatically controlled by a single-chip microcomputer.

The biological chip hybridization system provided in the present invention can also use the temperature control device to increase or reduce the temperature of the sample solution in the hybridization chip in a programmed manner of increasing or reducing the temperature or keep the temperature constant, resulting not only in shorter hybridization duration, improved hybridization efficiency, but also integration of the cleaning and drying functions, so that a full-automatic operation of hybridization reaction, cleaning and drying can be achieved, and thus such biological chip hybridization system is valuable for popularization.

DETAILED EMBODIMENTS

A biological chip hybridization system is disclosed by the present invention, which can be achieved by properly improving the technological parameters by those skilled in the art with reference to the contents herein. Specifically, it should be noted that all similar substitution and modification are obvious to those skilled in the art, all of which are deemed to be included in the present invention. The product, application method and application of the present invention have been described by preferred examples, and it is obvious that modification, or proper change and combination can be made to the method and application described herein by those skilled in the art, without departing from the contents, spirit and scope of the present invention, in order to achieve and apply the techniques disclosed in the present invention.

The present invention will be further illustrated in combination with specific examples below, in order to make the technical solution of the present invention better understood by those ordinary skilled in the art.

Example 1

Figure 1:
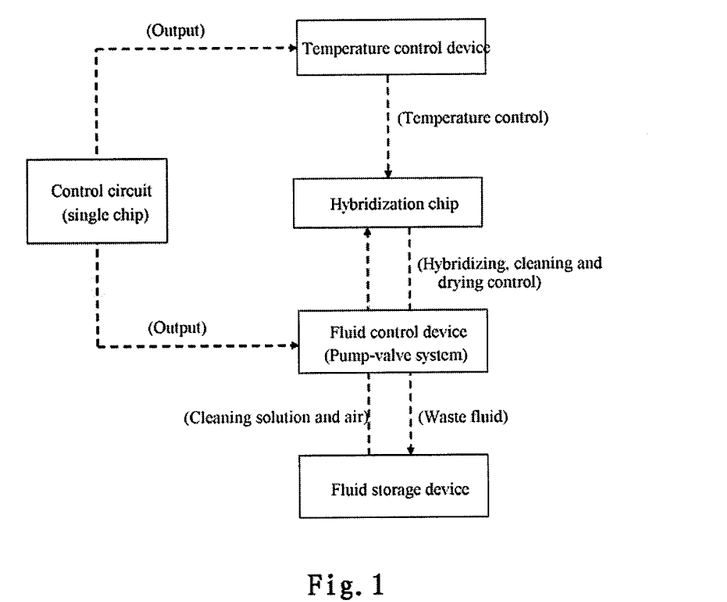
FIG. 1 is a schematic diagram showing the components of the biological chip hybridization system according to the present invention.
Figure 2:
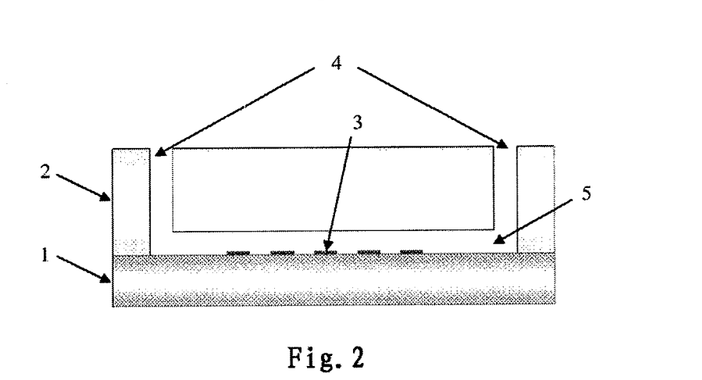
FIG. 2 is a structural representation of the bio-chip of the biological chip hybridization system according to the present invention, wherein 1 is the substrate; 2 is the cover plate; 3 is the bio-probe array; 4 is the through hole; and 5 is the hybridization chamber.

A biological chip hybridization system for single sample hybridization is provided in this example, consisting of: a bio-chip, two fluid channels respectively connected to both through holes on the bio-chip, the fluid control device connected to the fluid channel, control circuit, temperature control device and fluid storage device. Wherein, instruction is given by the control circuit to the temperature control device, so that the temperature of the chip and the sample solution can be automatically controlled; instruction is also given by the control circuit to the fluid control device, so as to automatically control the fluid in the chip hybridization, cleaning and drying process. Driven by the pump valve device, the cleaning liquid and air are added from the fluid storage device to the hybridization chamber through the fluid channel, and then discharged to the waste storage device through the fluid channel. A schematic diagram of the biological chip hybridization system according to the present invention is shown in FIG. 1, and each component is described in detail as follows:

FIG. 2 is a structural representation of the bio-chip of the biological chip hybridization system according to the present invention, wherein 1 is the substrate of the bio-chip; 2 is the cover plate of the bio-chip; 3 is the bio-probe array on the substrate; 4 is the through hole of the bio-chip; and 5 is the hybridization chamber. Said two through holes are respectively connected to two fluid channels.

Figure 3:
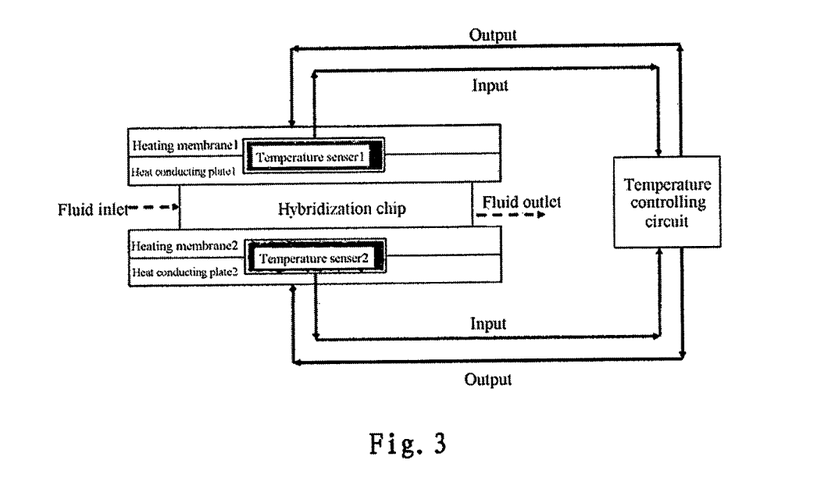
FIG. 3 is a schematic diagram showing the temperature control device of the biological chip hybridization system according to the present invention.

A schematic diagram of the temperature control device of the biological chip hybridization system according to the present invention is shown in FIG. 3. The bio-chip is placed between two heat-conducting plates, with each heat-conducting plate heated by the heating membrane. The temperature of the heat-conducting plate is detected in real time by the temperature sensor and input to the temperature control circuit, and the program set by the temperature control circuit is output to the heating membrane, so as to automatically control the temperature of the hybridization chip.

Figure 4:
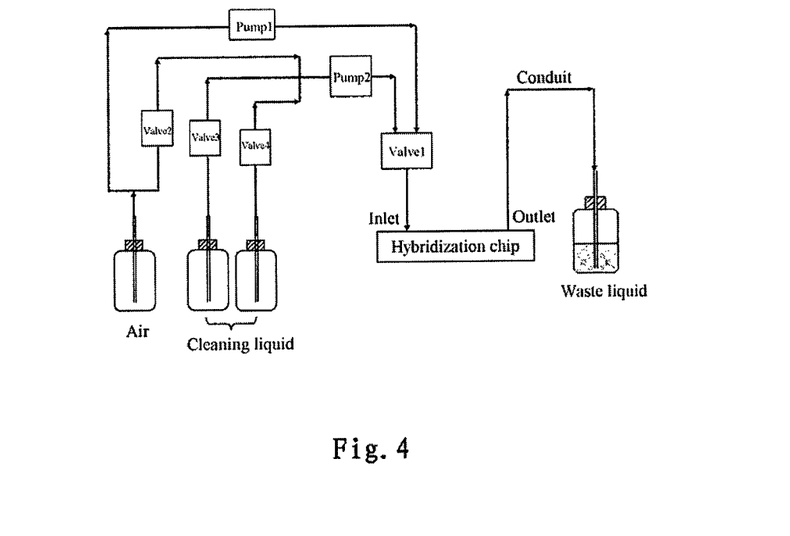
FIG. 4 is a schematic diagram showing the fluid control device of the biological chip hybridization system according to the present invention.

The fluid control device and the fluid storage device of the biological chip hybridization system according to the present invention are shown in FIG. 4. The fluid control device comprises two pumps, four electromagnetic valves and a conduit, wherein pump 1 is used for controlling the sample reciprocating flow dynamic hybridization process in the hybridization chip, with one end directly connected to the air via the pipe, while the other end connected to the through hole of the bio-chip via valve 1; pump 2 is used to control the cleaning and drying processes, with one end connected to the air via valve 2, and simultaneously to the cleaning liquid bottle via valve 3 and valve 4, while the other end connected to the through hole of the chip via valve 1; the other through hole of the chip is connected to the waste liquid bottle through the other fluid channel. Valves 2, 3 and 4 are two-way valves, wherein valves 3 and 4 are used to control the connection and disconnection of the flow path of the cleaning liquid in the cleaning process, while valve 2 is used to control the connection and disconnection of air path in the drying process. Valve 1 is three-way valve, which is used to control the connection and disconnection of any of the flow paths of both pump 1 and pump 2, with its common end connected to the chip inlet.

Example 2

A biological chip hybridization system for single sample is provided in this example. As different from Example 1, the bio-chip is a reciprocating flow based bio-chip, with its structure shown in FIG. 5, wherein 1 is the substrate; 2 is the cover plate; 3 is the bio-probe array; 4 is the through hole; 5 is the hybridization chamber; 6 is the microfluidic channel; and 7 is the microfluidic layer.

Figure 5:
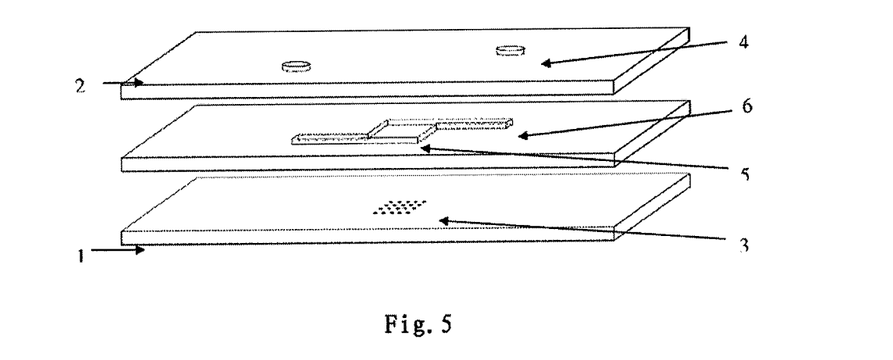
FIG. 5 is a structural representation of the bio-chip provided in Example 2 for the biological chip hybridization system according to the present invention, wherein 1 is the substrate; 2 is the cover plate; 3 is the bio-probe array; 4 is the through hole; 5 is the hybridization chamber; 6 is the microfluidic channel; and 7 is the microfluidic layer.

The bio-chip is formed by three layers including the cover plate, the microfluidic layer and the substrate through sealing. The cover plate 2 is hydrophilic with two through holes 4 disposed for the entrance and exit of the solution. After chemical modification, the lower surface of cover plate 2, i.e., the interface to the microfluidic layer, has a static contact angle of 15 degrees to water, while the upper surface, after hydrophobic treatment, has a static contact angle of 100 degrees to water; the thickness of the microfluidic layer 7 is about 0.2 mm, on which the hollow-out hybridization chamber 5 and the microfluidic channel 6 are disposed, with one end of the microfluidic channel 6 connected to the hybridization chamber 5, and the other end to the through hole 4 of the cover plate 2; the upper surface of the microfluidic layer 6 is sealed with the lower surface of the cover plate 2, and the lower surface of the microfluidic layer 7 is sealed with the substrate 1 so that a reciprocating flow hybridization chip is formed. The hybridization chamber 5 is connected to the bio-probe array 3, the shape and area of which correspond to those of the bio-probe array 3. Substrate 1 can be a glass-based DNA chip or a protein chip.

Example 3

The operational procedures for the biological chip hybridization system described in Example 1 or Example 2 are as follows:

After the sample solution is loaded at the through hole on the bio-chip, two fluid channels are respectively connected to two through holes on the bio-chip. The temperature of the hot plate is adjusted to 60° C. Subsequently, the hybridization step is started with pump 1 open, and then the flow path where pump 1 is located is opened by the three-way valve 1 so that the sample solution is driven to move back and forth inside the chamber of the hybridization chip to allow for dynamic hybridization; after the completion of the hybridization, pump 1 and valve 1 are closed and the chip temperature is adjusted to 42° C. Subsequently, the cleaning step is started with both pump 2 and valve 3 open, so that the first cleaning liquid is driven into the chip for cleaning. After that, valve 3 is closed while valve 4 is open, so that the second cleaning liquid is driven into the chip for cleaning. After the completion of the cleaning step, valve 4 is closed while valve 2 is open, and the drying step is started to drive the air into the chip and discharge the waste liquid from the chip to the waste liquid bottle. Finally, the chip surface is completely blow-dried. After hybridization, the chip is taken out and detected by scanning on LuxScan scanner.

Specific experiment conditions are as follows: the chip used is maize gene chip; the molecular structure of the probe is $NH_2$-(T)GCACTCGCACAACCCAAGAACCT; the probe concentration is 2 µmol/L, while the sample concentration is 1 nmol/L with a loading volume of 63 µL, and the molecular structure is Cy5-TCAGCGACGCCATCAGGT-TCTTGGGTTGTGCGAGAGAGATTGGGGAT GCA; the flow rate of the reciprocating flow during hybridization is 0.1 mL/min, and the hybridization duration is 10 min; during cleaning, the flow rate of the cleaning liquid is 3 mL/min and the cleaning duration is 2 min; during drying, the air flow rate is 100 mL/min, and the duration for blow-drying is 5 min.

Figure 6:
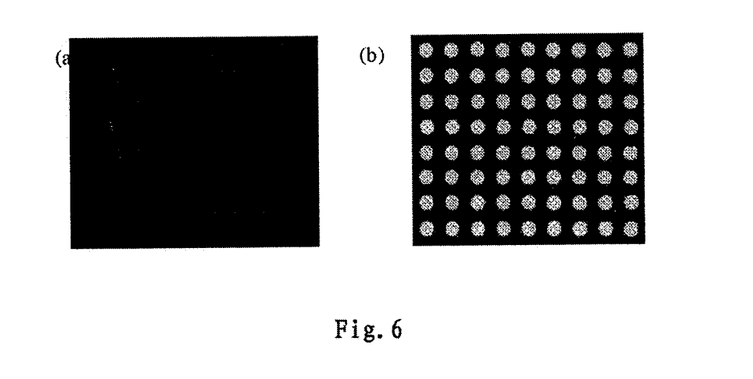
FIG. 6 is the hybridization experiment results for the maize gene chip of the biological chip hybridization system according to the present invention, (a) the fluorescent micrograph before hybridization; (b) the fluorescent micrograph after hybridization.

FIG. 6 is the fluorescent micrographs of the hybridization chip. As shown in FIG. 6a, there is no fluorescent signal of the probe array before hybridization; after treating by the biological chip hybridization system according to the present invention, very strong fluorescent signal appears with high inter-dot uniformity and the inter-dot signal variation less than 10%, suggesting significantly high hybridization efficiency, as shown in FIG. 6b.

Example 4

Figure 7:
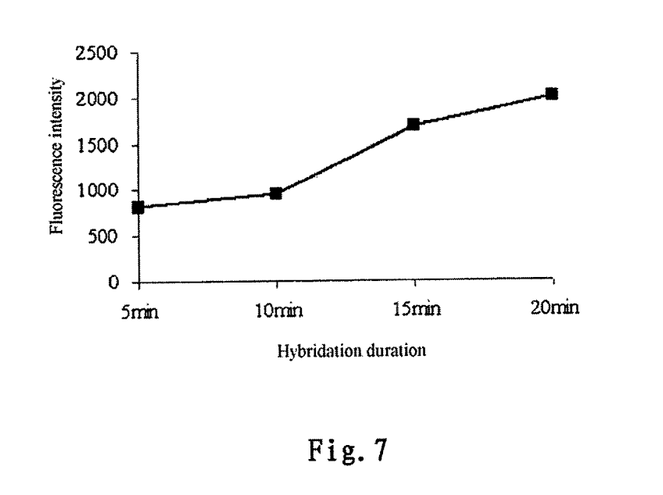
FIG. 7 is a plot of fluorescence intensity v.s. hybridization duration, under the same sample concentration.

The hybridization procedure and the experiment conditions of the biological chip hybridization system are similar to those in Example 3, with the differences that the sample concentration is 0.1 nmol/L, and the hybridization duration is 5 min, 10 min, 15 min and 20 min, respectively. The hybridization results are shown in FIG. 7. Under the same sample concentration, the fluorescent signal intensity increases with increased hybridization duration.

Example 5

Figure 8:
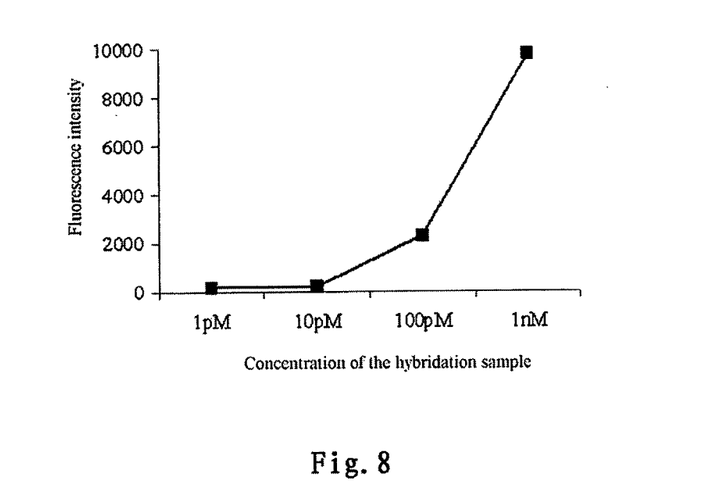
FIG. 8 is a plot of fluorescence intensity v.s. sample concentration, under the same hybridization duration.

The hybridization procedure and the experiment conditions of the biological chip hybridization system are similar to those in Example 3, with the differences that the sample concentration is 1 pmol/L, 10 pmol/L, 100 pmol/L and 1000 pmol/L, respectively. The hybridization results are shown in FIG. 8. Under the same hybridization duration, the fluorescent signal intensity increases with increased sample concentration.

Example 6

The hybridization procedure and the experiment conditions of the biological chip hybridization system according to the present invention are similar to those in Example 3, with the differences that the chip and reagent used are Jingxin nine genetic deafness gene detection kit provided by CapitalBio corporation; the sample concentration is 10 nmol/L with a loading volume of 65 µL; the hybridization temperature is 50° C., the flow rate of the reciprocating flow is 5 µL/min, and the hybridization duration is 15 min; the cleaning temperature is 42° C., the flow rate of the cleaning liquid is 2 mL/min, and the cleaning duration is 2 min; the drying temperature is 42° C., the air flow rate is 100 mL/min, and the duration for blow-drying is 5 min. Specific experiment conditions are as follows: the chip and reagent used are Jingxin nine genetic deafness gene detection kit provided by CapitalBio corporation; the sample concentration is 10 nmol/L with a loading volume of 65 μL; the hybridization temperature is 50° C., the flow rate of the reciprocating flow is 5 μL/min, and the hybridization duration is 15 min; the cleaning temperature is 42° C., the flow rate of the cleaning liquid is 2 mL/min, and the cleaning duration is 2 min; the drying temperature is 42° C., the air flow rate is 100 mL/min, and the duration for blow-drying is 5 min.

Figure 9:
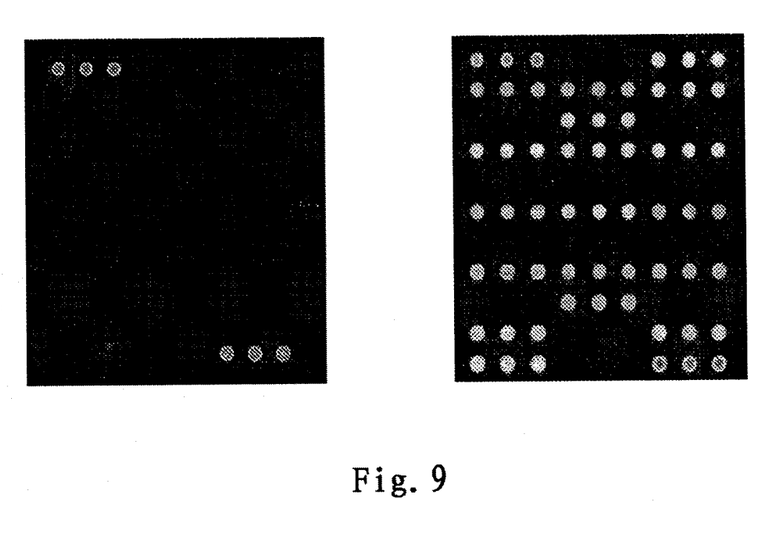
FIG. 9 is the hybridization experiment results for the deafness chip of the biological chip hybridization system according to the present invention, (a) the fluorescent micrograph before hybridization; (b) the fluorescent micrograph after hybridization.

The hybridization results are shown in FIG. 9. The fluorescent scanning image of the probe array before hybridization is shown in FIG. 9a, in which only the reference points have fluorescent signal, whereas other sample points have no fluorescent signal. After the hybridization, cleaning and drying treatment of the full-automatic hybridization system, the fluorescent image is shown in FIG. 9b, in which except for the reference points, all sample points exhibit very strong fluorescent signals with high inter-dot uniformity and the inter-dot signal variation less than 10%, suggesting significantly high hybridization efficiency.

The examples described above are only the preferred examples of the present invention, and the scope of the present invention can not be limited thereto. All modifications to the temperature control mode and the fluid control mode according to the spirit of the present invention fall within the scope of the present invention.

A biological chip hybridization system provided in the present invention have been described by way of examples, and it is obvious that modification or proper change and combination can be made to the biological chip hybridization system according to the present invention by those skilled in the art, without departing from the contents, spirit and scope of the invention, in order to achieve the techniques disclosed in the present invention. Specifically, it should be pointed out that all similar substitutions and modifications are obvious to those skilled in the art, and they are deemed to be within the spirit, scope and contents of the present invention.

The invention claimed is:

1. A biological chip hybridization system, comprising:
   a bio-chip, which comprises a substrate with probe array and a cover plate with at least two through holes, wherein a hybridization chamber is formed between the substrate and the cover plate;
   at least two fluid channels, which are connected to the hybridization chamber respectively through said two through holes; and
   a fluid control device, which is connected to the fluid channel,
   wherein the bio-chip further comprises a microfluidic layer disposed between the cover plate and the substrate, wherein the microfluidic layer has the hybridization chamber and at least two hollow-out microfluidic channels, with one end of each microfluidic channel connected to the hybridization chamber, and the other end connected to one through hole of the cover plate, respectively, and the hybridization chamber of the microfluidic layer connected to the bio-probe array of the substrate,
   wherein the surface of the cover plate contacted with the microfluidic layer has a contact angle of less than 90 degrees with respect to water, and the other surface of the cover plate has a contact angle of 90 to 180 degrees with respect to water.

2. The biological chip hybridization system according to claim 1, characterized in that the fluid control device comprises at least one pump for providing gas pressure, and one valve for controlling the entrance of the fluid, and the pump is connected to the fluid channel through the valve.

3. The biological chip hybridization system according to claim 1, characterized in that the probe of the bio-chip is selected from any one of the group consisting of DNA, RNA, PNA, LNA, peptide and protein.

4. The biological chip hybridization system according to claim 1, characterized in that the material for the cover plate of the bio-chip is selected from the group consisting of glass, silicon and polymers.

5. The biological chip hybridization system according to claim 4, characterized in that the polymer is selected from the group consisting of polymethyl methacrylate, polydimethyl siloxane, polycarbonate, polyethylene terephthalate and cycloolefin copolymers.

6. The biological chip hybridization system according to claim 1, characterized in that the material for the substrate of the bio-chip is selected from the group consisting of glass, silicon and polymers.

7. The biological chip hybridization system according to claim 6, characterized in that the polymer is selected from the group consisting of polymethyl methacrylate, polydimethyl siloxane, polycarbonate, polyethylene terephthalate and cycloolefin copolymers.

8. The biological chip hybridization system according to claim 1, characterized in that the biological chip hybridization system further comprises a temperature control device.

9. The biological chip hybridization system according to claim 8, characterized in that the temperature control device comprises hot plate, heating body, cooling body, temperature sensor and temperature controller.

10. The biological chip hybridization system according to claim 9, characterized in that the material for the hot plate is selected from the group consisting of metal, alloy, silicon, and glass.

11. The biological chip hybridization system according to claim 9, characterized in that the heating body is selected from the group consisting of resistance wire, resistance membrane and Peltier device.

12. The biological chip hybridization system according to claim 9, characterized in that the cooling body is selected from the group consisting of radiator fan and semiconductor refrigerator device.

13. The biological chip hybridization system according to claim 9, characterized in that the material for the hot plate is silicon or glass.

14. The biological chip hybridization system according to claim 1, characterized in that the biological chip hybridization system further comprises a fluid storage device connected to the fluid channel.

15. The biological chip hybridization system according to claim 14, characterized in that the fluid storage device is a container, or a chip with fluid cavity.

16. The biological chip hybridization system according to claim 14, characterized in that the fluid storage device is a glass bottle or a plastic bottle.

17. The biological chip hybridization system according to claim 1, characterized in that the biological chip hybridization system further comprises a control circuit.

18. The biological chip hybridization system according to claim 17, characterized in that the control circuit is a single-chip microcomputer system.

19. The biological chip hybridization system according to claim 1, characterized in that the biological chip hybridization system further comprises a monitor.

20. The biological chip hybridization system according to any of claim 1, characterized in that the cross-sectional area of the microfluidic channel of the microfluidic layer is in the range of 0.01 to 10 mm$^2$, and the length is in the range of 1 mm to 100 mm.

* * * * *